US006969496B2

(12) United States Patent
Vetter et al.

(10) Patent No.: US 6,969,496 B2
(45) Date of Patent: Nov. 29, 2005

(54) APPARATUS WITH INCREASED YIELD AND SELECTIVITY USING SIDE-BY-SIDE REACTION ZONES

(75) Inventors: Michael J. Vetter, Schaumburg, IL (US); Paul R. Cottrell, Arlington Heights, IL (US); Joseph E. Zimmermann, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 668 days.

(21) Appl. No.: 10/180,832

(22) Filed: Jun. 24, 2002

(65) Prior Publication Data

US 2002/0164278 A1 Nov. 7, 2002

Related U.S. Application Data

(62) Division of application No. 09/458,854, filed on Dec. 10, 1999, now Pat. No. 6,472,577.

(60) Provisional application No. 60/112,588, filed on Dec. 17, 1998.

(51) Int. Cl.[7] .............................. B01J 8/02; C07C 5/333
(52) U.S. Cl. ...................... 422/221; 422/219; 422/214; 422/232; 422/236
(58) Field of Search ................................ 422/221, 214, 422/219, 232, 236

(56) References Cited

U.S. PATENT DOCUMENTS

| 3,652,231 | A | | 3/1972 | Greenwood et al. ....... 23/288 G |
|---|---|---|---|---|
| 3,692,861 | A | * | 9/1972 | Chikatsu et al. ............. 585/810 |
| 3,745,112 | A | | 7/1973 | Rausch ........................ 208/139 |
| 3,927,987 | A | * | 12/1975 | Winter et al. ................ 422/200 |
| 3,978,150 | A | | 8/1976 | McWilliams, Jr. ........ 260/683.3 |
| 3,981,792 | A | | 9/1976 | Scott ............................ 208/49 |
| 4,218,287 | A | | 8/1980 | Albright et al. ............... 201/9 |
| 4,430,517 | A | | 2/1984 | Imai et al. ................... 585/660 |
| 5,053,572 | A | | 10/1991 | Kim et al. ................... 585/441 |
| 5,378,350 | A | * | 1/1995 | Zimmermann et al. ..... 208/136 |
| 6,057,485 | A | | 5/2000 | Merrill et al. ............... 585/449 |
| 6,194,626 | B1 | * | 2/2001 | Vora et al. ................... 585/326 |
| 6,218,589 | B1 | * | 4/2001 | Cottrell ....................... 585/324 |
| 6,271,428 | B1 | * | 8/2001 | Cottrell ....................... 585/259 |
| 6,472,577 | B1 | * | 10/2002 | Zimmermann et al. ..... 585/441 |
| 6,884,400 | B1 | * | 4/2005 | Austin et al. ................ 422/216 |

\* cited by examiner

Primary Examiner—N. Bhat
(74) Attorney, Agent, or Firm—John G. Tolomei; James C. Paschall

(57) ABSTRACT

An apparatus provides for increased feed throughput without loss of conversion or selectivity by increasing the catalyst volume in a final reactor of at least three reaction zones. The catalyst volume of the final reactor may be larger because the inner and outer screens that define a radial flow bed are extended. A low LHSV is maintained by increasing the catalyst volume in the final reactor.

13 Claims, 3 Drawing Sheets

APPARATUS WITH INCREASED YIELD AND SELECTIVITY USING SIDE-BY-SIDE REACTION ZONES

CROSS-REFERENCE TO RELATED APPLICATIONS

This application is a Division of application Ser. No. 09/458,854 filed Dec. 10, 1999 now U.S. Pat. No. 6,472,577, which application claims priority from Provisional Application Ser. No. 60/112,588 filed Dec. 17, 1998, the contents of which are hereby incorporated by reference.

FIELD OF THE INVENTION

The field of art to which this invention pertains is the dehydrogenation of hydrocarbons in multiple reaction zones that use on stream catalyst replacement.

BACKGROUND OF THE INVENTION

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. One example of this process is the dehydrogenation of isobutane to produce isobutylene which can be polymerized to provide tackifying agents for adhesives, viscosity-index additives for motor oils, and impact-resistant and antioxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 (Imai et al) discusses a dehydrogenation process and catalyst for use therein.

Most catalysts for the dehydrogenation of hydrocarbons are susceptible to deactivation over time. Deactivation will typically occur because of an accumulation of deposits that block active pore sites or catalytic sites on the catalyst surface. Where the accumulation of coke deposits causes the deactivation, reconditioning the catalyst to remove coke deposits restores the activity of the catalyst. Coke is normally removed from the catalyst by contact of the coke-containing catalyst with an oxygen-containing gas at a high enough temperature to combust or remove the coke in a regeneration process. In a moving bed process, the regeneration process is carried out by removing catalyst from the vessel in which the hydrocarbon conversion is taking place and transporting the catalyst to a separate regeneration zone for coke removal. Arrangements for continuously or semi-continuously removing catalyst particles from a bed in a reaction zone for coke removal in a regeneration zone are well known. U.S. Pat. No. 3,652,231 describes a continuous catalyst regeneration process which is used in conjunction with the catalytic reforming of hydrocarbons, the teachings of which are hereby incorporated by reference. In the reaction zone of U.S. Pat. No. 3,652,231, the catalyst is transferred under gravity flow by removing catalyst from the bottom of the reaction zone and adding catalyst to the top while reactants flow cross currently through a radial flow bed.

In the past, flow-related phenomena have limited mass flow and fluid velocity through the radial flow beds. One phenomenon, known as "pinning," inhibits catalyst transfer in many reactor arrangements. Pinning occurs when the flow of fluid at sufficient velocity blocks the downward movement of catalyst. Pinning is a function of the gas composition, the gas velocity, the physical characteristics of the catalyst, and the physical characteristics of the flow channel through which the catalyst must move. As the gas flows through the channels that retain the catalyst, the gas impacts the catalyst particles and raises intergranular friction between the particles. When the vertical component of the frictional forces between the particles overcomes the force of gravity on the particles, the particles become pinned. As the flow path length of gas through the catalyst particles becomes longer, the forces on the particles progressively increase from the outlet to the inlet of the flow channel.

Another flow-limiting phenomena is called "void blowing". Void blowing occurs when the gas velocity displaces from a surface of the catalyst bed across which it flows from the screen or other retaining elements, thereby creating a void space. The rapid circulation or churning of catalyst over the free surface of the void space can abrade or break catalyst particles, resulting in the production of reduced size particles or fines. This fine material can plug the catalyst bed, exacerbate the void blowing problem, or accumulate in other process piping or equipment in a manner that interferes with the continued effective operation of the process.

As technology has improved and problems such as pinning and void blowing have been better understood, it has been possible to increase the fluid velocity through the radial flow beds of existing reaction zones that were previously limited by these fluid flow phenomena. Increasing the velocity or throughput is of course desirable because it permits an increase in capacity with only minor operating changes to the existing equipment. However, it has been found that further increases in the capacity of many existing dehydrogenation units cannot only be obtained with decreases in conversion or selectivity of the products produced. The limitations in conversion and/or selectivity are related to the reduced time that results from the higher fluid velocity through the catalyst beds. The catalyst contact time is typically expressed in terms of the liquid hourly space velocity (LHSV) of the feed through the catalyst bed. Higher LHSV's may be compensated for, to some extent, by an increased reaction temperature which raises the catalyst activity. Although compensating for higher throughput by increasing the reactor temperatures may maintain conversion levels, it is typically at the expense of lower selectivity and increased coke production on the catalyst.

The most direct way to overcome the problems of space velocity limitations is to add more catalyst to the process. Increasing the catalyst volume is readily accomplished in the design stage for a new unit. Unfortunately for existing units, adding additional catalyst could require expensive modification or replacement of all of the reactors and the associated piping for the delivery of reactants and the transfer of catalyst between the reactors.

Accordingly, it is an objective of this invention to increase the throughput of existing dehydrogenation reactors with only limited modifications to the reaction zone and the associated piping.

BRIEF SUMMARY OF THE INVENTION

It has now been surprisingly discovered that it is possible to increase throughput in a dehydrogenation process, for example, without sacrificing the conversion or selectivity by increasing the catalyst volume in the last reaction zone. Adding catalyst to the last reaction zone effectively decreases the overall LHSV for the feed stream at higher throughput rates. As a result, conversion is maintained without increasing the temperature in any of the individual reactors and thereby avoiding any fall off in selectivity or increase in coke production. The apparatus includes multiple reactors wherein the final reactor is in a side-by-side arrangement to the upstream reactors. furthermore, the larger capacity of the final reactor may comprise taller inner and outer screens for retaining a larger catalyst bed therebetween.

One embodiment of the present invention may be characterized as a reactor system including a series of reactors. The reactor system comprises a first reactor for contacting a feed with a first catalyst bed in the first reactor, at least one intermediate reactor for contacting an effluent from the first reactor with an intermediate catalyst bed in the intermediate reactor(s) and a final reactor for contacting an intermediate effluent from a last one of the intermediate reactor(s) with a final catalyst bed in the final reactor. A transfer line is included for adding catalyst to the top of the final catalyst bed and for withdrawing catalyst from the bottom of the final catalyst bed in the final reactor. The final reactor is located to the side of the intermediate reactor(s). The catalyst bed of the final reactor has an inner and outer screen retaining the final catalyst bed therebetween for the radial flow of reactants. The final catalyst bed retains at least 5% greater volume of catalyst than is retained in the first catalyst bed.

Extending the inner and outer screens increases the volume of the catalyst with a corresponding decrease in the LHSV of the process. The catalyst volume will usually be increased by an amount that will keep the LHSV of the process below about 4 hrs$^{-1}$. Increasing the catalyst volume in the final reactor will also result in the local LHSV of the first reactor and any intermediate reactor being greater than the LHSV of the final reactor. Of course, any decrease in the LHSV will be limited by the amount of catalyst that can be added to the modified reactor. Preferably, the final reactor will increase the catalyst volume by 10% and, more preferably, the catalyst volume will increase by 15% or more. Structural limitations such as foundation support may control the amount of catalyst that may be added to the final reaction zone by extension of the inner and outer screens.

Other embodiments of the present invention encompass further details of preferred process conditions and reactor modification methods.

DETAILED DESCRIPTION OF THE INVENTION

Figure 1:
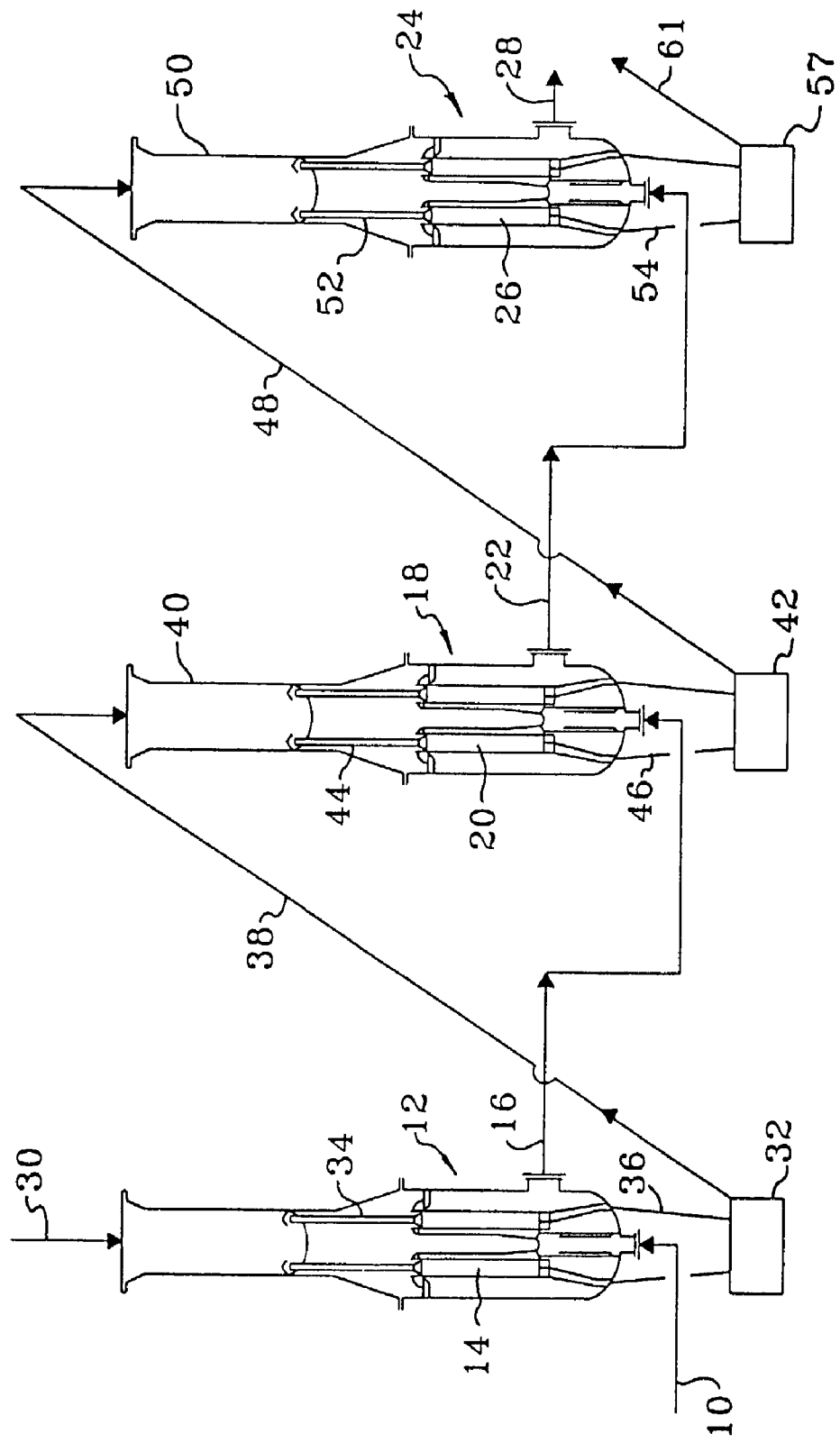
FIG. 1 is a schematic drawing of a series of dehydrogenation reactors.

The dehydrogenation of paraffinic hydrocarbons is well known to those skilled in the art of hydrocarbon processing. In the dehydrogenation process, fresh hydrocarbon feed is combined with recycle hydrogen and unconverted hydrocarbons. Dehydrogenatable hydrocarbons for this invention will preferably include isoalkanes having 3 or 5 carbon atoms. A suitable feed of dehydrogenatable hydrocarbons will often contain light hydrocarbons (i.e., those having less carbon atoms than the primary feed components) which, for the purpose of this invention, serve as contaminants. In most cases, olefins are excluded from the dehydrogenation zone recycle in order to avoid the formation of dienes which produce unwanted by-products in many of the olefin conversion processes. Along with the dehydrogenatable hydrocarbons, the feed to the dehydrogenation zone of the present invention comprises an $H_2$-rich stream, preferably containing at least 75 mol-% $H_2$. The $H_2$ acts to suppress the formation of hydrocarbonaceous deposits on the surface of the catalyst, more typically known as coke, and can act to suppress undesirable thermal cracking. Because $H_2$ is generated in the dehydrogenation reaction and comprises a portion of the effluent, the $H_2$-rich stream introduced into the reaction zone generally comprises recycle $H_2$ derived from separation of the dehydrogenation zone effluent. Alternately, the $H_2$ may be supplied from suitable sources other than the dehydrogenation zone effluent.

The combined stream of hydrogen and hydrocarbons is passed through a suitable bed of dehydrogenation catalyst maintained at the proper dehydrogenation conditions such as temperature, pressure and space velocity, and the effluent from the catalytic reaction zone is processed further to yield a stream of olefinic hydrocarbons. The dehydrogenation reactors of this invention preferably comprise at least a last radial flow reactor through which the catalytic composite gravitates downwardly to allow a substantially continuous replacement of the catalyst with fresh and/or regenerated catalyst. A detailed description of the moving bed reactors herein contemplated may be obtained by reference to U.S. Pat. No. 3,978,150. The dehydrogenation reaction is a highly endothermic reaction which is typically effected at low (near atmospheric) pressure conditions. The precise dehydrogenation temperature and pressure employed in the dehydrogenation reaction zone will depend on a variety of factors such as the composition of the paraffinic hydrocarbon feedstock, the activity of the selected catalyst, and the hydrocarbon conversion rate. In general, dehydrogenation conditions include a pressure of from about 0 to about 35 bars and a temperature of from about 480° C. (900° F.) to about 760° C. (1400° F.). A suitable hydrocarbon feedstock is charged to the reaction zone and contacted with the catalyst contained therein at an LHSV of from about 1 to about 10. Hydrogen, principally recycle hydrogen, is suitably admixed with the hydrocarbon feedstock in a mole ratio of from about 0.1 to about 10. Preferred dehydrogenation conditions, particularly with respect to $C_4$–$C_5$ paraffinic hydrocarbon feedstocks, include a pressure of from about 0 to about 5 bars and a temperature of from about 540° C. (1000° F.) to about 705° C. (1300° F.), a hydrogen-to-hydrocarbon mole ratio of from about 0.1 to about 2, and, after employment of this invention, an LHSV of less than 4.

The dehydrogenation zone of this invention may use any suitable dehydrogenation catalyst. Generally, the preferred catalyst comprises a platinum group component, an alkali metal component, and a porous inorganic carrier material. The catalyst may also contain promoter metals which advantageously improve the performance of the catalyst. It is preferable that the porous carrier material of the dehydrogenation catalyst be an absorptive high surface area support having a surface area of about 25 to about 500 m$^2$/g. The porous carrier material should be relatively refractory to the conditions utilized in the reaction zone and may be chosen from those carrier materials which have traditionally been utilized in dual function hydrocarbon conversion catalyst. A porous carrier material may, therefore, be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxides such as alumina, titanium dioxide, zirconium dioxides, magnesia, silica alumina, alumina boria, etc.; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as theta alumina, give the best results in general. The preferred catalyst will have a theta alumina carrier which is in the form of spherical particles having relatively small diameters on the order of about 1/16-inch. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or an elemental metal or in combination with one or more other ingredients of the catalyst. The platinum group component generally comprises from about 0.01 to about 2 wt-% of the final catalytic composite with a preferred platinum content of about 0.1 and 1 wt-%. When present, the preferred alkali metal is normally either potassium or lithium, depending on the feed hydrocarbon. The concentration of the alkali metal may range from about 0.1 to 5 wt-%. The preferred promoter metal is tin and normally constitutes about 0.01 to about 1 wt-%. It is preferred that the atomic ratio of tin to platinum be between 1:1 and about 6:1. The tin component may be incorporated into the catalytic composite in any suitable manner known to effectively disperse this component in a very uniform manner throughout the carrier material. A more detailed description of the preparation of the carrier material and the addition of the platinum component and the tin component to the carrier material may be obtained by reference to U.S. Pat. No. 3,745,112.

Operation of the dehydrogenation zone will produce a mixture of hydrogen and hydrocarbons. Normally, a portion of the hydrocarbons will include an equilibrium mixture of the desired isoolefin and its isoalkane precursor. The effluent from the dehydrogenation reaction section passes to a hydrogen recovery section. This separation section removes hydrogen from the effluent and recovers it in high purity for recycle to the dehydrogenation reaction section. Separation steps for the removal of hydrogen will normally include cooling and compressing with subsequent cooling and flashing in a separation vessel. Such methods for the separation of hydrogen and light gases are well known by those skilled in the art.

A typical dehydrogenation process passes the combined hydrocarbon and hydrogen feed through a plurality of reactors with interstage heating between the reactors. This invention is generally applicable to dehydrogenation processes having three or more reaction zones. The feed hydrocarbons and hydrogen are initially heated by indirect heat exchange with the effluent from the dehydrogenation zone. Following heating, the feed mixture normally passes through a heater to further increase the temperature of the feed components before it enters the dehydrogenation reactor where it is contacted with the dehydrogenation catalyst. The endothermic reaction reduces the temperature of the reactants which then undergo interstage heating before entering the next reactor. After heat exchange with the feed, the effluent from the last dehydrogenation zone effluent passes to product separation facilities.

DETAILED DESCRIPTION OF THE DRAWINGS

FIG. 1 shows a simplified flow path for reactants and catalyst in a dehydrogenation process having three reactors. Additional details of heat exchangers, inter-heaters, fluidization piping for catalyst transfer, instrumentation, and other equipment are omitted. Line 10 passes the combined feed to first reactor 12 that contains first catalyst bed 14. The feed passes in radial flow through bed 14 and exits reactor 12 through line 16. Line 16 carries the effluent from the first reactor through an interstage heater (not shown) that reheats the effluent from reactor 12 before it enters single intermediate reactor 18 that contains catalyst bed 20. The effluent from the first reaction zone passes again in radial flow through bed 20 and an intermediate effluent stream exits reactor 18 via line 22. Line 22 passes the feed though another interstage heater (not shown) and to final reactor 24 for radial flow through final catalyst bed 26. Line 28 recovers the effluent from catalyst bed 26 for separation in separation facilities (not shown).

Looking next at the flow of catalyst, catalyst supply line 30 delivers fresh catalyst to a reduction zone that prepares the freshly regenerated catalyst for passage through reaction zones 12, 18, and 24. Periodic withdrawal of catalyst from collector 32 prepares reactor 12 for incremental transport of catalyst downwardly through reactor bed 14 via catalyst transfer lines 34 and 36. Catalyst lifted from collector 32 passes to reactor 18 via line 38 that drops catalyst into surge hopper 40. Surge hopper 40, in a manner similar to that described for reactor 12, retains catalyst in preparation for passage through bed 20 and into collector 42 via catalyst transfer lines 44 and 46. Similar to that described in connection with reactor 18, catalyst transfer line 48 transfers catalyst from collector 42 to surge hopper 50 for the supply of catalyst to reactor 24. Catalyst passes through bed 26 via catalyst transfer lines 52 and 54 before passing into surge hopper 57. Line 61 withdraws catalyst from surge hopper 57 for regeneration in regeneration facilities (not shown).

Figure 2:
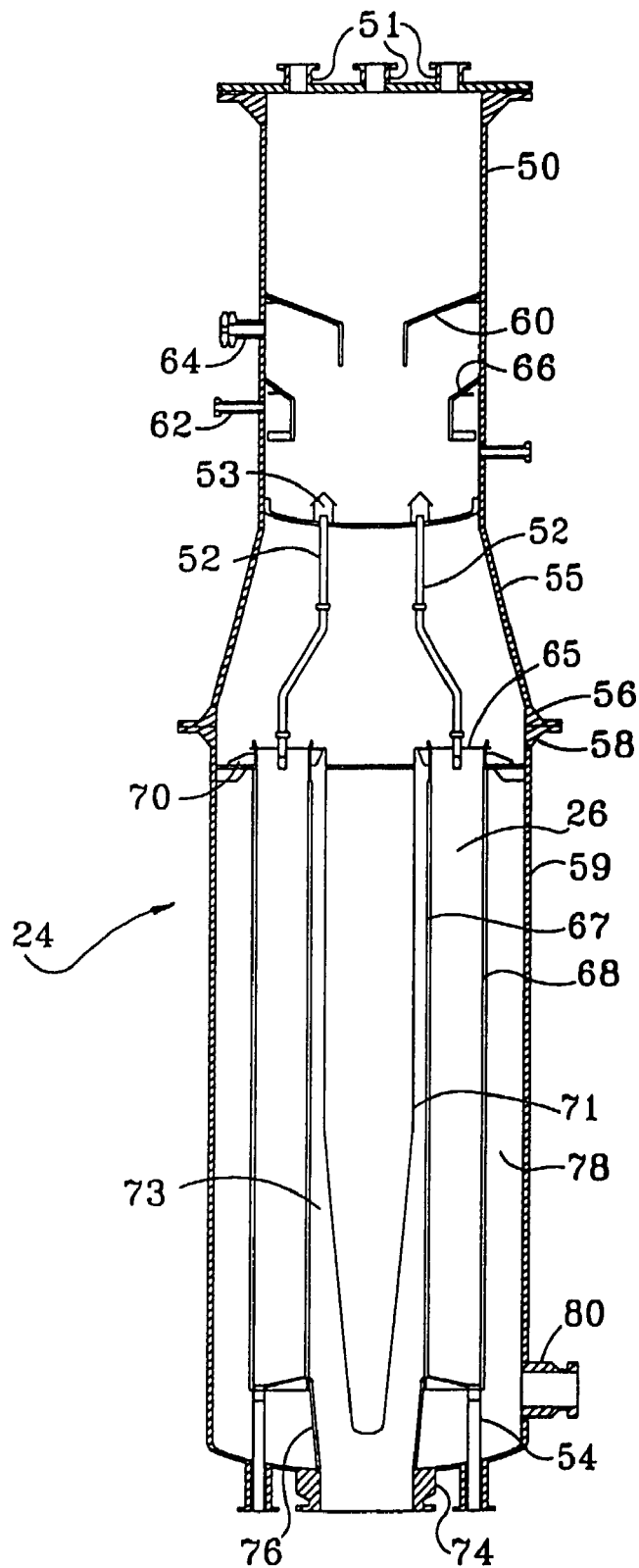
FIG. 2 is a schematic drawing of a single dehydrogenation reactor.

Additional internal details of reactor 24 are shown in FIG. 2. Surge hopper 50 is fixed above reactor shell 59 to frusto-conical reducer 55. A pair of flanges 56 and 58 connect frusto-conical reducer 55 to reactor shell 59. Upper baffle 60 operates in conjunction with nozzles 62 and 64 to control the movement of catalyst through the surge hopper. Baffle 66 distributes gas entering through nozzle 62 while nozzle 64 controls the withdrawal of gas from a lower portion of surge hopper 50. Catalyst enters the top of surge hopper 50 through upper nozzles 51. Catalyst exits the bottom of the surge hopper across covered inlets 53 of catalyst transfer lines 52. Catalyst transfer lines 52 discharge catalyst particles across cover plates 65 into annular bed 26 as catalyst is withdrawn from the bottom of bed 26 via catalyst transfer lines 54.

Inner screen 67 and outer screen 68 retain annular catalyst bed 26 and at least partially define boundaries of distribution space 73 and collection space 78. Outer screen section 68 is supported from bracket 70 through attachment to an upper portion of the vessel wall that forms reactor shell 59. Inner screen 67 is fixed with respect to outer screen 68 for support thereof. Central distributor plug 71 occupies the central portion of reactor 24 surrounded by inner screen 67 and serves to distribute incoming reactants while minimizing the volume of distribution space 73. Reactants enter bottom nozzle 74 through closed conduit section 76 that extend to the bottom of inner screen 67. Conduit 76 may contain expansion elements as necessary to accommodate differential expansion between screens 67 and 68 and reactor shell 59. Collection space 78 to the outside of screen 68 serves as a collection zone that supplies the reactor effluent for discharge through nozzle 80.

Figure 3:
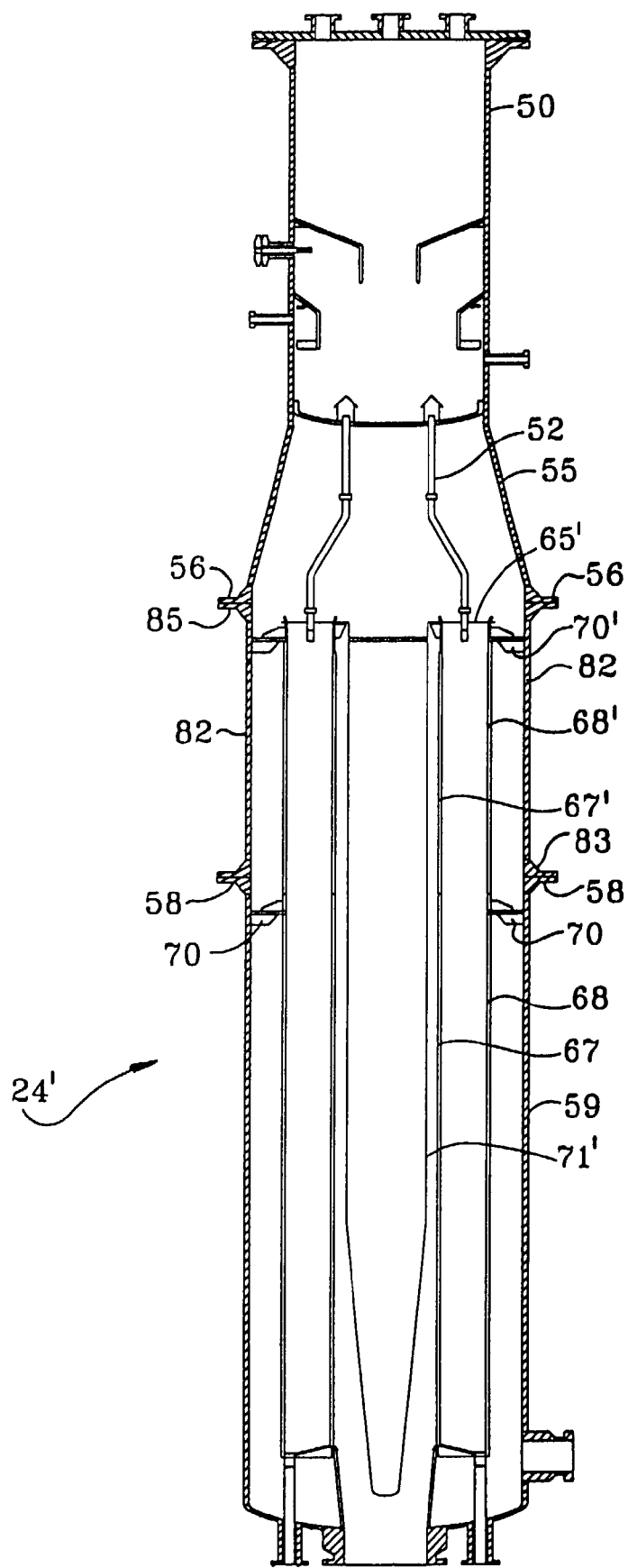
FIG. 3 is a schematic drawing showing a modified dehydrogenation reactor.

FIG. 3 shows reactor 24 modified in accordance with this invention to add approximately 50% more catalyst to the annular bed of the reactor. To effect this modification, surge hopper 50 was removed by separating flanges 58 and 56. Surge hopper 50 and reducer 55 were removed together along with transfer lines 52.

With surge hopper 50 and its associated equipment removed, temporarily, the cover plate assemblies at the top of existing screens 67 and 68 were removed to permit extension of the screens by the addition of inner screen extension 67' and outer screen extension 68'. Screen extensions 67' and 68' contain cover plate arrangement 65' at the top sections of the screens. Extended distributor plug 71' was inserted into the central space bounded by screen extensions 67' and inner screen 67. Distributor plug 71' as well as the inner screens and outer screens are supported by support bracket 70' fixed to the wall of vessel extension section 82. Existing support brackets 70 undergo minor modification to now serve as additional guide brackets.

The existing inner screen and outer screen sections may be extended by welding new screen sections of the same diameter to the top of the existing screens. Welding can be facilitated through the use of backing bars or other solid members that may be added to the top of the screens or available as part of the cover plate assembly. Stiffeners and other longitudinal supports may be carried through from the existing screens to the new screens as necessary.

Vessel extension 82 has lower flange 83 and upper flange 85. Flange 58 receives flange 83 for a simple sealed connection of additional vessel section 82. Flange 85 in turn receives flange 56 of existing hopper 50 and reducer 55 to provide a completed enclosure for screen extensions 67' and 68'. As surge hopper 50 is put back in place, catalyst transfer lines 52 are received by new cover plate arrangement 65'.

The new surge hopper section and the extended screens were provided without disturbing the lower section of reactor 24 in any manner. Only minor modifications were necessary at the top of the reactor to provide additional guides that are useful in controlling the placement and location of the screens within reactor 24'. As a result, the additional throughput for the unit is achieved with a relatively quick modification using components that are easily fabricated prior to any field modification. Prior fabrication of the modified internals has a further advantage of minimizing downtime for the process when making changes to the reactor.

EXAMPLE

A three-reactor dehydrogenation process was evaluated using a simulation of the dehydrogenation process to verify the advantages and performance from the modification of a single third reactor to retain a higher catalyst volume. The simulation was first performed to evaluate the three-reactor system for processing 41,420 barrels per day of a dehydrogenation feed through the three reaction zones at an LHSV of 4.8 hrs$^{-1}$. The process used a hydrogen-to-hydrocarbon ratio of 0.4 and the predicted operation was based on the performance of a platinum aluminum type catalyst containing a potassium modified and a tin promoter. The inlet temperatures through the three reaction zones were 632°, 642°, and 643° C., respectively. The base case showed a conversion of 48.3 wt-% with a selectivity of 83.5 wt-%.

In following the method of this invention, the catalyst volume of the third reactor was increased by 50% through an increase in screen length of from 40 feet to 60 feet. The overall increase in the catalyst volume was approximately 19%. The overall LHSV with the modified reactor dropped to 4.0 hrs$^{-1}$. The remaining operating parameters remained the same as for the base case. Evaluation of the performance showed an increase in conversion to 50.4 wt-% and an increase in selectivity to 83.8 wt-%.

What is claimed is:

1. A reactor system including a series of reactors, the reactor system comprising:
    a first reactor for contacting a feed with a first catalyst bed in the first reactor,
    at least one intermediate reactor for contacting an effluent from the first reactor with an intermediate catalyst bed in the at least one intermediate reactor; and
    a final reactor for contacting an intermediate effluent from a last one of the at least one intermediate reactor with a final catalyst bed in the final reactor, a transfer line for adding catalyst to the top of the final catalyst bed and a transfer line for withdrawing catalyst from the bottom of the final catalyst bed in the final reactor, the final reactor being located to the side of the at least one intermediate reactor and the catalyst bed of the final reactor having an inner and outer screen retaining the final catalyst bed therebetween for the radial flow of reactants, said outer screen being extended to a distance that will increase the volume of catalyst at least 5% greater than the first catalyst bed.

2. The reactor system of claim 1 including only a single intermediate reactor.

3. The reactor system of claim 1 wherein one of the LHSV of the first reactor and the LHSV of all intermediate reactors is greater than the LHSV of the final reactor.

4. The reactor system of claim 3 wherein the LHSV of the first reactor and the LHSV of all of the intermediate reactors is greater than the LHSV of the final reactor.

5. The reactor system of claim 1 wherein one of the LHSV of the first reactor and the LHSV of one of the intermediate reactors is greater than the LHSV of the final reactor.

6. The reactor system of claim 1 wherein a volume of the catalyst bed in the final reactor is at least 10% greater than the volume of the catalyst bed in the first reactor.

7. A reactor system for the dehydrogenation of hydrocarbons comprising:
    a first reactor for contacting a dehydrogenation feed with a first catalyst bed in the first reactor,
    at least one intermediate reactor for contacting an effluent from the first reactor with an intermediate catalyst bed in the at least one intermediate reactor; and
    a final reactor for contacting an intermediate effluent from a last one of the at least one intermediate reactor with a final catalyst bed in the final reactor, a transfer line for adding catalyst to the top of the final catalyst bed and a transfer line for withdrawing catalyst from the bottom of the final catalyst bed in the final reactor while contacting the intermediate effluent with the final catalyst bed of the final reactor, the final reactor being located to the side of the intermediate reactor and the catalyst bed of the final reactor having an inner and outer screen retaining the final catalyst bed therebetween for the radial flow of reactants, said outer screen being extended to a distance that will increase the volume of catalyst at least 5% greater than the first catalyst bed.

8. The reactor system of claim 7 including only a single intermediate reactor.

9. The reactor system of claim 7 wherein one of the LHSV of the first reactor and the LHSV of all intermediate reactors is less than the LHSV of the final reactor.

10. The reactor system of claim 9 wherein the LHSV of the first reactor and the LHSV of all of the intermediate reactors is less than the LHSV of the final reactor.

11. The reactor system of claim 7 wherein one of the LHSV of the first reactor and the LHSV of one of the intermediate reactors is less than the LHSV of the final reactor.

12. The reactor system of claim 7 wherein a volume of the catalyst bed in the final reactor is at least 10% greater than the volume of the catalyst bed in the first reactor.

13. A reactor system including a series of reactors, the reactor system comprising:

a first reactor for contacting a feed with a first catalyst bed in the first reactor, the first catalyst bed being retained between an inner and outer screen for the radial flow of reactants, at least one intermediate reactor for contacting an effluent from the first reactor with an intermediate catalyst bed in the at least one intermediate reactor; and a final reactor for contacting an intermediate effluent from a last one of the at least one intermediate reactor with a final catalyst bed in the final reactor, a transfer line for adding catalyst to the top of the final catalyst bed and a transfer line for withdrawing catalyst from the bottom of the final catalyst bed in the final reactor, the final reactor being located to the side of the at least one intermediate reactor and the catalyst bed of the final reactor being retained between a final inner and outer screen for the radial flow of reactants, the final inner and outer screen being at least 5% taller than the first inner and outer screen.

\* \* \* \* \*